(12) United States Patent
Broaddus et al.

(10) Patent No.: US 9,669,198 B2
(45) Date of Patent: Jun. 6, 2017

(54) SYSTEM AND METHOD FOR INTRACRANIAL IMPLANTATION OF THERAPEUTIC OR DIAGNOSTIC AGENTS

(75) Inventors: William C. Broaddus, Midlothian, VA (US); Rahul Mahajan, Chester, VA (US); George T. Gillies, Charlottesville, VA (US)

(73) Assignees: University of Virginia Patent Foundation, Charlottesville, VA (US); Virginia Commonwealth University, Richmond, VA (US)

( * ) Notice: Subject to any disclaimer, the term of this patent is extended or adjusted under 35 U.S.C. 154(b) by 46 days.

(21) Appl. No.: 12/375,139

(22) PCT Filed: Jul. 18, 2007

(86) PCT No.: PCT/US2007/016256
§ 371 (c)(1),
(2), (4) Date: Jan. 27, 2009

(87) PCT Pub. No.: WO2008/013709
PCT Pub. Date: Jan. 31, 2008

(65) Prior Publication Data
US 2009/0192487 A1    Jul. 30, 2009

Related U.S. Application Data

(60) Provisional application No. 60/833,834, filed on Jul. 27, 2006.

(51) Int. Cl.
*A61M 31/00* (2006.01)
*A61B 90/11* (2016.01)
*A61B 6/00* (2006.01)

(52) U.S. Cl.
CPC ........... *A61M 31/007* (2013.01); *A61B 90/11* (2016.02); *A61B 6/508* (2013.01)

(58) Field of Classification Search
CPC ............ A61M 37/0069; A61M 31/007; A61B 19/201; A61B 6/508; A61B 90/11; A61B 90/14
(Continued)

(56) References Cited

U.S. PATENT DOCUMENTS 4,757,128 A   7/1988   Domb et al.
4,789,724 A   12/1988  Domb et al.
(Continued)

FOREIGN PATENT DOCUMENTS

DE        29612100       9/1996
EP        0427358        5/1991
WO     WO 2008/013709    1/2008

OTHER PUBLICATIONS

P. Sampath, H. Brem, Implantable Slow-Release Chemotherapeutic Polymers for the Treatment of Malignant Brain Tumors, Cancer Control Journal. 5, 1998.
(Continued)

*Primary Examiner* — Kami A Bosworth
(74) *Attorney, Agent, or Firm* — Robert J. Decker; Tanner IP, PLLC

(57) ABSTRACT

A system and related method for delivering the anti-tumoral agent carmustine or other types of diagnostic or therapeutic agents into the brain of a patient with a brain tumor includes an insertion device, a skull mount, and a reformulated geometry of the carmustine compound (or other material) optimized for use in the insertion device and for maximized biodegradation time. The insertion device may be front loaded with the carmustine material (or other material) and inserted through the mount on a skull, to the location of the brain tumor, where the carmustine (or other material) is then released. It should be appreciated that the diagnostic and/or therapeutic system and related method thereof are not necessarily limited to the brain of a subject. It may also be used (Continued)

in the organ structures or tubular structures, as well as portions and locations thereof.

74 Claims, 19 Drawing Sheets

(58) Field of Classification Search
USPC ..... 604/57–64, 158, 164.01, 164.04, 164.12, 604/170.02
See application file for complete search history.

(56) References Cited

U.S. PATENT DOCUMENTS

| | | | |
|---|---|---|---|
| 5,004,457 A * | 4/1991 | Wyatt et al. | 604/158 |
| 5,643,286 A | 7/1997 | Warner et al. | |
| 5,776,144 A | 7/1998 | Leysieffer et al. | |
| 6,203,526 B1 * | 3/2001 | McBeth et al. | 604/96.01 |
| 6,217,557 B1 * | 4/2001 | Hakansson et al. | 604/167.06 |
| 6,478,790 B2 * | 11/2002 | Bardani | 604/891.1 |
| 6,752,812 B1 | 6/2004 | Truwit | |
| 6,902,569 B2 | 6/2005 | Parmer et al. | |
| 2002/0052610 A1 | 5/2002 | Skakoon et al. | |
| 2002/0111603 A1 * | 8/2002 | Cheikh | 604/891.1 |
| 2005/0131386 A1 * | 6/2005 | Freeman et al. | 604/522 |
| 2005/0245896 A1 | 11/2005 | Kucharczyk et al. | |

OTHER PUBLICATIONS

M. S. Lesniak, H. Brem, Targeted Therapy for Brain Tumours, Nature Reviews 3 (2004) 499-508.

C. Guerin et al., Recent advances in brain tumor therapy: local intracerebral drug delivery by polymers, Investigational New Drugs. 22 (2004) 27-37.

M. S. Lesniak et al., Drug Delivery to Tumors of the Central Nervous System, Current Neurology and Neuroscience Reports 1 (2001) 210-216.

Gliadel® Wafer package insert, MGI Pharma Inc., accessed Apr. 2010.

P. Wang, J. Frazier, H. Brem, Local Drug Delivery to the Brain, Advanced Drug Delivery Reviews 54 (2002) 987-1013.

R. Baker; Controlled Release of Biologically Active Agents. 1987 50-73.

A. Gopferich, J. Tessmar, Polyanhydride degradation and erosion. Advanced Drug Delivery Reviews 54 (2002) 911-931.

E. Sipos et al, Optimizing interstitial delivery of BCNU from controlled release polymers for the treatment of brain tumors, Cancer Chemother Pharmacal 39 (1997) 383-389.

The International Search Report corresponding to the PCT/US2007/16256 application.

U.S. Appl. No. 60/833,834, filed Jul. 27, 2006.

European Supplemental Search Report, Application No. 07810560.8, dated Sep. 21, 2011.

* cited by examiner

THE STRUCTURAL FORMULA FOR POLIFEPROSAN 20 IS:

RATIO: m:n = 20:80; RANDOM COPOLYMER

THE STRUCTURAL FORMULA FOR CARMUSTINE IS:

| INITIAL LENGTH ($l_0$) | ROD ($r_0$ = 0.5mm) $R^2$ VALUE | STRIP ($w_0$ = 5mm, $d_0$ = 1mm) $R^2$ VALUE |
|---|---|---|
| 15mm | 0.6508 | 0.9765 |
| 30mm | 0.6630 | 0.9816 |
| 60mm | 0.6690 | 0.9839 |
| 120mm | 0.6720 | 0.9850 |

SYSTEM AND METHOD FOR INTRACRANIAL IMPLANTATION OF THERAPEUTIC OR DIAGNOSTIC AGENTS

CROSS-REFERENCE TO RELATED APPLICATIONS

The present application is a national stage filing of International Application No. PCT/US2007/016256, filed Jul. 18, 2007, which claims benefit of priority under 35 U.S.C. §119(e) from U.S. Provisional Application Ser. No. 60/833,834, filed Jul. 27, 2006, entitled "Method and Means for Intracranial Implantation of Carmustine Anti-Tumoral Agents," the disclosure of which is hereby incorporated by reference herein in their entirety.

BACKGROUND OF THE INVENTION

Approximately 13,000 people develop new cases of brain tumors every year [1]. Of all central nervous system (CNS) tumors, nearly 42% are specifically diagnosed as Glioblastoma Multiforme (GBM). Conventional treatment consists of surgical resection and external beam radiation. The median survival for patients undergoing surgical resection alone is 6 months while those who undergo a more complete regimen including radiation is 9 months [2]. Thus the fact remains that even aggressive treatment with established methods of surgery, radiation, and chemotherapy leads to a median survival rate of less than one year for patients diagnosed with the condition [3].

In the case of chemotherapy, some of the apparent ineffectiveness may be explained by the unique environment of the brain. The brain is a complex and delicate organ; however, it is not entirely defenseless. The body is equipped with various mechanisms specific to the CNS designed to protect and isolate it. In attempting to treat brain tumors with chemotherapy, these very defenses can become barriers to effective treatment. The Blood Brain Barrier (BBB) results from the tight gap junctions of the brain's capillaries' endothelia. The consequence of this is to effectively reduce the permeability of the capillary walls to small ions and molecules and to almost completely block permeation of large molecules such as peptides. The only type of molecules which readily cross the barrier are small, electrically neutral and lipid soluble: qualities which does not describe most chemotherapeutic agents [2]. Furthermore, the brain capillary endothelium has a reduced number of pinocytic molecules which normally transport molecules across the cells into the brain and contain proteins which actually actively remove drug molecules before they can enter the brain. In addition to the BBB, the Blood Cerebrospinal fluid Barrier (BCB) and the Blood Tumor Barrier (BTB) also work to reduce the permeation of drugs into the brain. The BCB consists of tightly bound cells of the choroid epithelium. In addition to producing the cerebrospinal fluid (CSF), these cells are also capable of actively removing organic molecules from the CSF. The BTB results from the "leaky" vasculature often found inside tumors. This leads to a net outflow of fluid from the tumor and the resulting peritumoral edema. Such edema is results in partially or completely collapsed blood vessels in the tumor, further reducing the ability of chemotherapeutic agents in the blood to penetrate into the tumor.

Thus an overall effect of the BBB, BCB, and BTB is to limit the effectiveness of systemically administered chemotherapy. New chemotherapeutic agents such as angiogenesis inhibitors, cytokines, and others are so effectively excluded by such barriers that even when orally/intravenously administered in doses high enough to cause system toxicity, their concentrations within the brain and thus the brain tumor are too low to achieve significant tumorcidal activity.

Various strategies have arisen in order to circumvent these challenges in drug delivery. These include changing drug design to increase the drugs' permeability through the various barriers, temporarily disrupting the BBB, delivering the drug via catheters directly to the brain interstitium, delivering via convection-enhanced methods, and implanting drug releasing polymers or microchips directly at the site of the tumor. Gliadel® became the first new FDA approved therapy for patients with gliomas in 23 years. It provides an effective means of directly delivering the chemotherapeutic agent carmustine or BCNU (1,3-bis(2-chloroethyl)-1-nitroso-urea). The agent is incorporated into the polymer polifeprosan 20 or pCPP-SA (poly[bis(p-.carboxyphenoxy)propane.-co-sebacic acid]) at a 3.8% (wt/wt) concentration. FIG. 1 depicts the chemical structure of carmustine and polifeprosan, i.e., the structural formulas of polymer and drug (Prescribing info). Following tumor resection, these dime sized wafers are directly placed into the tumor cavity. Up to 8 of such dime-sized wafers are implanted into the cavity where they degrade over a period of approximately 3 weeks providing a long term sustained release of BCNU directly at the site of the tumor. FIG. 2 illustrates the wafers 31 being implanted. As shown, Gliadel Wafers are implanted in a tumor resection cavity 32 [2].

Such a method of sustained local delivery is especially appropriate because tumors resulting from recurrent GBM usually form within 2 cm of the resection site of the original tumor [1]. Thus Gliadel® was first approved for use as a treatment following resection of a GBM recurrence. It has since been shown to be effective as part of a primary response as well. In both cases the treatment was shown to raise the median survival rate significantly, as shown in FIGS. 3(A)-(B). The graphs represent the survival curves showing effect of Gliadel when used to treat tumor recurrence and when used with initial therapy [5]. The therapy adds local chemotherapy to the treatment plan without limiting radiation or any other traditional therapy.

Despite the benefit provided by Gliadel® therapy, there are limitations that remain to be overcome. Currently, patients only receive the wafers after tumor resection which requires major surgery involving an open craniotomy. Thus, even if a small tumor is detected early, the patient cannot receive local chemotherapy until the tumor has grown to a size which warrants resection. The wafers degrade over approximately 3 weeks [5]. Thus once they have dissolved, they cannot be replaced without a second open craniotomy.

SUMMARY OF THE INVENTION

Design of a minimally invasive instrumentation and methods for delivering such a treatment would address these limitations. Patients could thus begin to receive the benefits of chemotherapy earlier and this regimen could be re-administered with minor surgery to provide more than a single 3 week course. It is important to remember that a successful design will not guarantee realization of an ideal treatment; other limitations will exist such as choice of active agent but the limitations of physical delivery initially discussed would certainly be addressed by such a design. A successful design may thus be defined as one which causes minimal trauma to the patient compared to trauma caused by an open craniotomy (or procedure or treatment to other location or portion of the subject), allows accurate positioning of the wafer into the tumor, maintains desired wafer placement upon retraction of delivery instrument, provides for simple and intuitive manipulation by the surgeon, and is biocompatible/sterilizable.

In order to enable accurate placement of the carmustine wafers within the brain (or other location or portion of the subject) without necessitating open craniotomy, stereotactic techniques would have to be employed. Stereotaxis is a standard minimally invasive neurosurgical technique which allows surgeons to accurately guide instruments to parts of the brain through a small burr hole in the skull. One method involves the use of a rigid frame affixed to the patient's skull. Such a frame allows much more precise manipulation of the placement and angle of the instrument trajectory than would be possible freehand. However, a comparison was performed and a frameless stereotaxis system was instead chosen as the platform for this design. Frameless stereotaxis uses real time image guidance to ensure accurate placement of instruments and thus obviates the need for a rigid frame which causes further trauma by necessitating attachment to the skull. However, it should be appreciated that frame-based system may be used instead or in addition to.

An aspect of an embodiment of the present invention provides a system for intracranial delivery of a diagnostic or therapeutic solid agent to the brain of a subject. The system comprising: an insertion device for delivery of a diagnostic or therapeutic solid agent to the brain. The insertion device may be adapted to retain and release the diagnostic or therapeutic solid agent for delivery to the brain.

An aspect of an embodiment of the present invention provides a method for intracranial delivery of diagnostic or therapeutic solid agent to the brain of a subject. The method comprising: inserting a device for the delivery of a diagnostic or therapeutic solid agent to the brain. Further, the inserting may comprise retaining and releasing the diagnostic or therapeutic solid agent material for delivery to the brain.

An aspect of an embodiment of the present invention provides a system for intracranial delivery of a diagnostic or therapeutic solid agent to one or more locations of the subject. The system comprising: an insertion device for delivery of a diagnostic or therapeutic solid agent to the one or more locations of the subject. Further, the insertion device may be adapted to retain and release the diagnostic or therapeutic solid agent for delivery to the one or more locations of the subject.

An aspect of an embodiment of the present invention provides a method for intracranial delivery of diagnostic or therapeutic solid agent to one or more locations of a subject. The method comprising: inserting a device for the delivery of a diagnostic or therapeutic solid agent to one or more locations of the subject. Further, the inserting may comprise retaining and releasing the diagnostic or therapeutic solid agent material for delivery to the one or more locations of the subject.

It should be appreciated that the various embodiments of the present invention diagnostic and/or therapeutic system and related method thereof are not necessarily limited to the brain of a subject. It may also be used in the organ structures or tubular structures. An organ includes, for example, a solid organ, a hollow organ, parenchymal tissue (e.g., stomach, brain, esophagus, colon, rectum, kidneys, liver, etc.) and/or stromal tissue. Hollow organ structures includes, for example, stomach, esophagus, colon, rectum, and ducts, or the like. A tubular structure may include a blood vessel. A blood vessel may include one or more of the following: vein, venule, artery, arterial, or capillary.

Further, various embodiments of the present invention method and system may be directed to or communicated with one or more locations of the subject, such as, but not limited to one or more locations of the organ, tubular structure, etc.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware.

Moreover, it should be appreciated that any of the components or modules referred to with regards to any of the present invention embodiments discussed herein, may be a variety of materials and/or composites as necessary or required.

Still further, it should be appreciated that any of the components or modules (or combination thereof) may provide shape, size and volume contoured by adjusting its geometry and flexibility/rigidity according to the target location or anatomy (or region, including structure and morphology of any location) being treated.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF THE INVENTION

Figure 1:
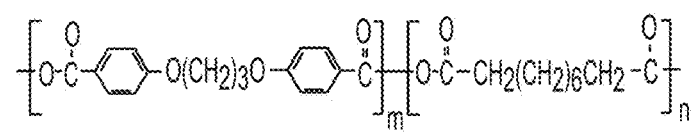
FIG. 1 provides the structural formulas for polifeprosan 20 and carmustine.
Figure 1:
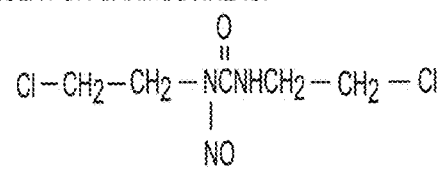
Figure 2:
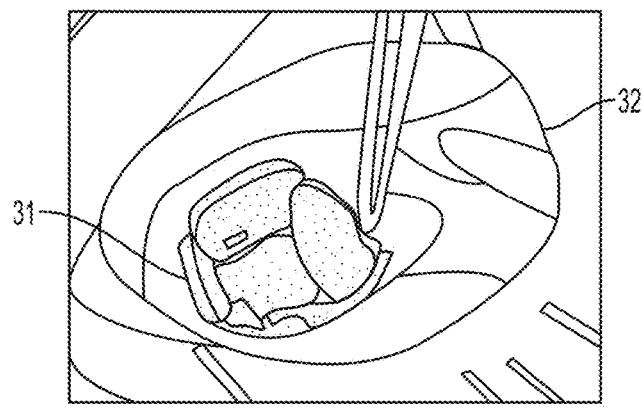
FIG. 2 provides a photographic depiction of a screenshot of Gliabel wafers implanted in a tumor resection cavity [2].
Figure 3A:
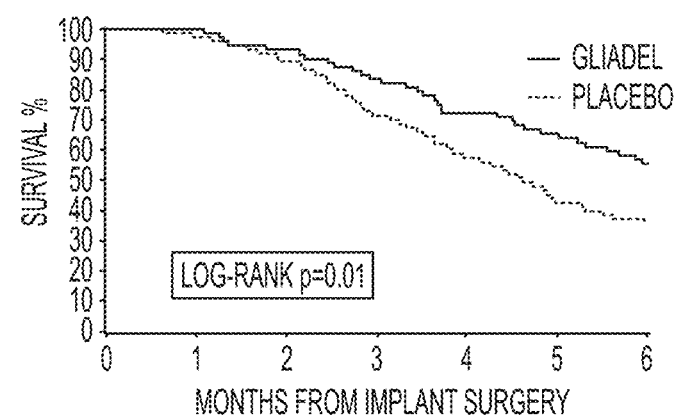
FIGS. 3(A)-(B) provide graphical representations of the survival curves showing the effect of Gliadel® when used to treat tumor recurrence and when used with initial therapy.
Figure 3B:
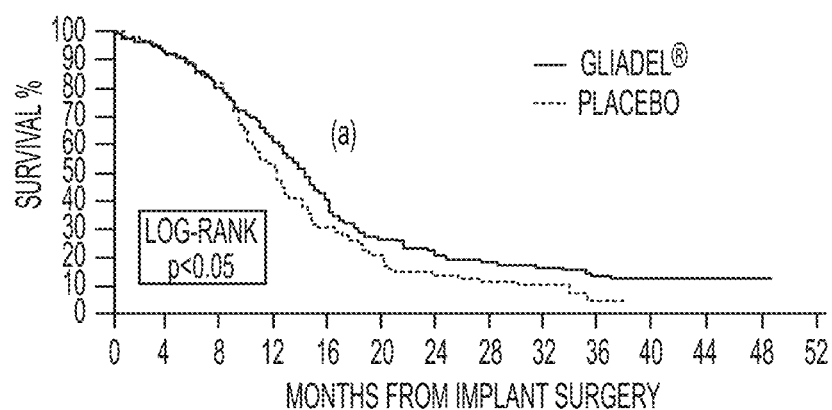
Figure 4A:
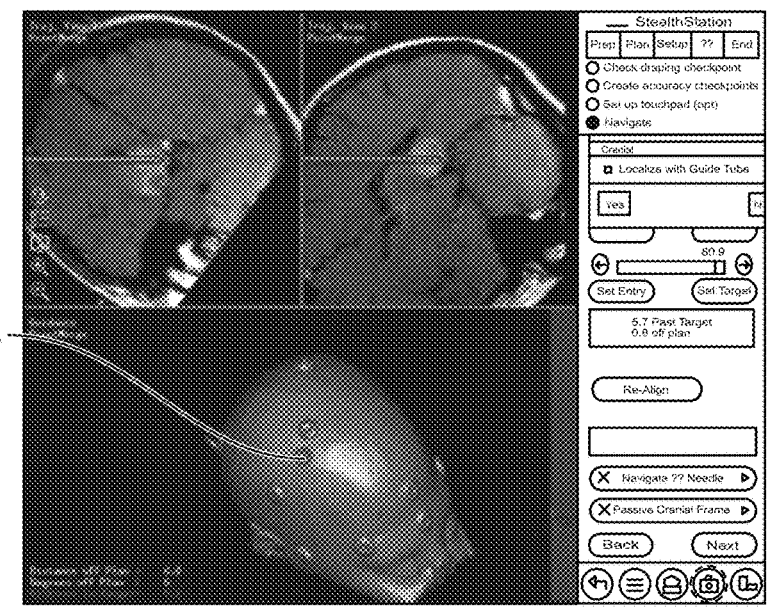
FIGS. 4(A)-4(B) provide a photographic depiction of the StealthStation® Treatment Guidance System by Medtronic.
Figure 4B:
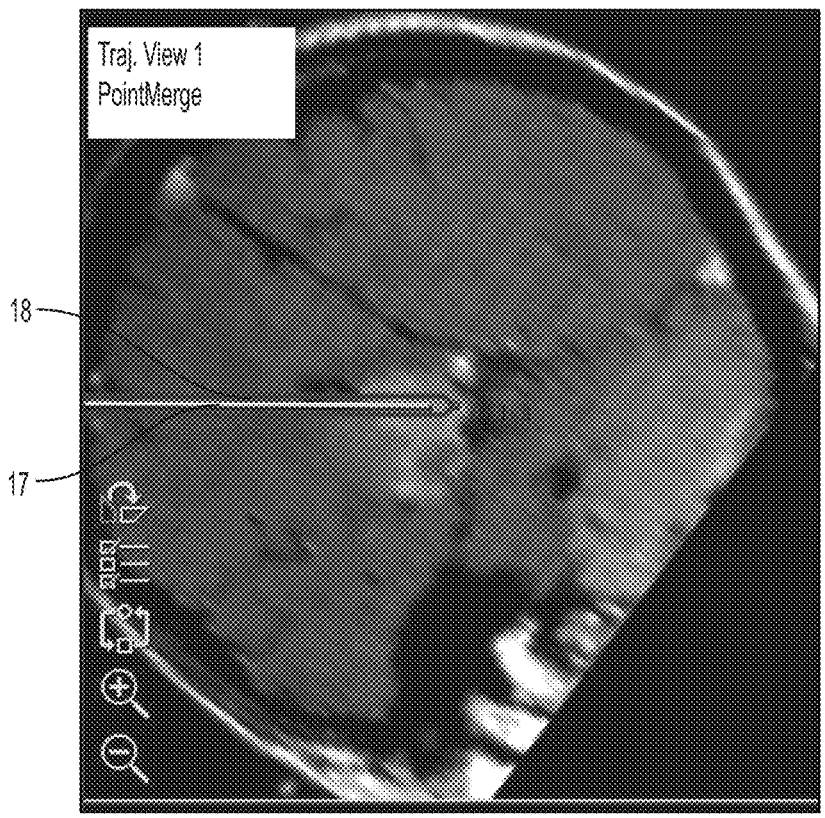

In frameless stereotaxis, the patient's head is immobilized and fiducials or markers which are visible to an infrared image guidance system are placed at reference points on the patient's skull and on the instruments entering the brain. Thus the guidance system can track the position of the instruments relative to the immobilized head. Surgeons can then visualize this information as it is coupled with preoperative MRI or CAT scan images of the brain and displayed on a monitor, as shown in FIG. 4(A)-(B). FIG. 4(A)-(B) are photographic depiction of screenshots from the StealthStation® Treatment Guidance System by Medtronic. In FIG. 4(A), reference points on the skull are visible. Also, the dot 16 on the skull shows the point of entry with the trajectory pointed directly towards the screen. Upper panes show MRI cross section images in planes which intersect to form the line containing the desired trajectory. FIG. 4(B) is a close up of the upper left pane from FIG. 4(A). The progress of the needle/instrument 17 down the path of the desired trajectory 18 can be seen. A small burr hole is created in the skull and a small trajectory guide is screwed in to the skull around it. Instruments may thus be guided along the desired trajectory into the brain.

The minimally invasive platform selected is most often used to guide instruments such as biopsy needles, electrodes, catheters/shunts, or neuroendoscopes into the brain. The system must be adapted for wafer delivery. At this point a problem emerges. Gliadel® wafers have a disk shaped geometry with dimensions of 14.5 mm diameter and 1 mm thickness. Thus the smallest profile or cross-section of the wafer would be a rectangle 14 mm by 1 mm. Delivering such a wafer would require a trajectory which cuts a 14 mm swath through brain tissue. This would cause far too much trauma to brain tissue and is simply clinically infeasible; the geometry of the wafer must be changed to allow for a smaller profile. Changing the wafer geometry would have an effect on the release of the drug. It therefore became necessary to develop a mathematical model in order to predict the expected release profile of the drug as the as the geometry and dimensions of the wafer were changed. With the idea of minimizing unknowns, the ideal dimensions are defined as those which allow the selected geometry to most closely approximate the release from already approved Gliadel® wafers. Thus the ideal reformulated wafer should release the same amount of drug as the Gliadel® wafers, over a similar length of time with a similarly shaped release curve The polymer pCPP-SA undergoes surface degradation [6]. Thus for slab-like geometries where surface area remains almost constant even as the wafer degrades, a theoretical zero order release can be expected. An initial model therefore attempted to predict the release of the drug simply based on surface degradation of the wafer. Degradation was characterized by a parameter "v" which is defined to be the rate at which the surface of the wafer recedes and has units mm/day. Thus:

$$-v = \frac{\partial r}{\partial t} \text{ and } -2v = \frac{\partial h}{\partial t} \quad (1)$$

where r=radius of the disk, h=thickness of the disk, t=time (in days). Because the wafer degrades at top and bottom surfaces, the height dimension decreases at twice the rate of the radius. Integrating the above with respect to time yields:

$$r_{(t)} = r_o - vt \text{ and } h_{(t)} = h_o - 2vt \quad (2)$$

For a disk, Volume is given by:

$$\text{Vol} = \pi r^2 h \quad (3)$$

Substituting from (2):

$$\text{Vol}_{(t)}=\pi(r_o-vt)^2(h_o-2vt) \quad (4)$$

Figure 5A:
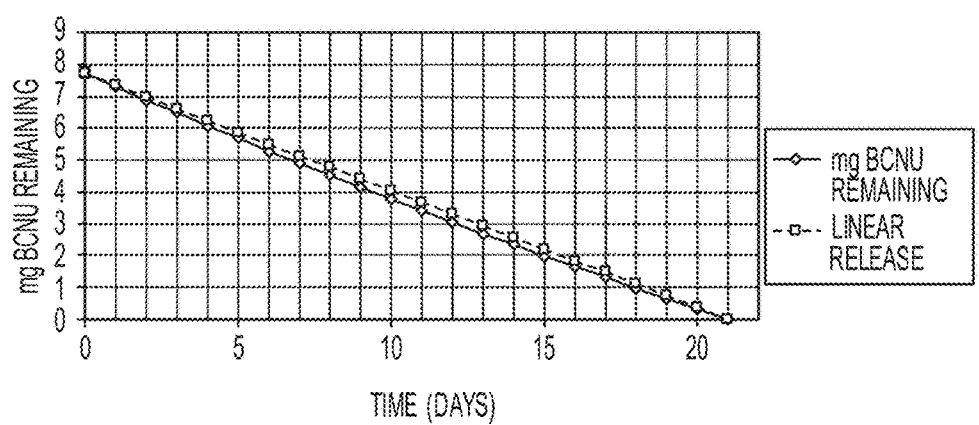
FIG. 5(A) provides a graphical representation of the degradation release model used to predict release from a Gliadel® wafer.

Because very little data is available about physical characteristics and properties of Gliadel® wafers, the parameter v had to be estimated from experimental data. It is known that the wafers degrade over approximately 3 weeks. Thus the dimensions of the commercial Gliadel® wafer could be substituted for $r_o$ and $h_o$ and the value of v is calculated such that the wafer's volume goes to zero in 21 days. Because the drug is homogeneously distributed throughout the wafer and this model assumes all drug release is controlled by degradation of the wafer, simply multiplying the initial mass of drug (7.7 mg) with the volume fraction of wafer remaining at any time t gives the mass of drug remaining in the wafer. FIG. 5A graphically illustrates the degradation release model used to predict release from a Gliadel® wafer. A line showing perfectly linear release of the entire mass of drug over 21 days is provided for comparison. It is evident that the slab-like disk geometry of the wafer is expected to degrade very linearly ($R^2$=0.9936).

Having created the model based on known properties of Gliadel® wafer, the model could then be applied to other geometries to predict their release profiles. The first alternate geometry considered was of course the rod. The profile of a rod most closely resembles that of instruments normally used to enter the interstitium in stereotactic neurosurgery. It thus provides the cost advantage of being able to use traditional instruments such as catheters and needles to aid in its delivery. However, linear release is dependent on an almost constant surface area during degradation which only occurs for slab-like geometries. Due to this concern of nonlinear release from a rod, a second geometry of a thin strip was also investigated. Such a geometry would more closely resemble a slab where most of the degradation occurs on two primary surfaces.

For a rod, the same equation as that used to model a disk may be used with, of course, different values for $r_o$ and $h_o$. A similar model for the volume of a strip having initial dimensions of length $l_o$, width $w_o$, and thickness $d_o$ is:

$$\text{Vol}_{(t)}=(l_o-2vt)(w_o-2vt)(d_o-2vt) \quad (5)$$

Figures 5B, 6:
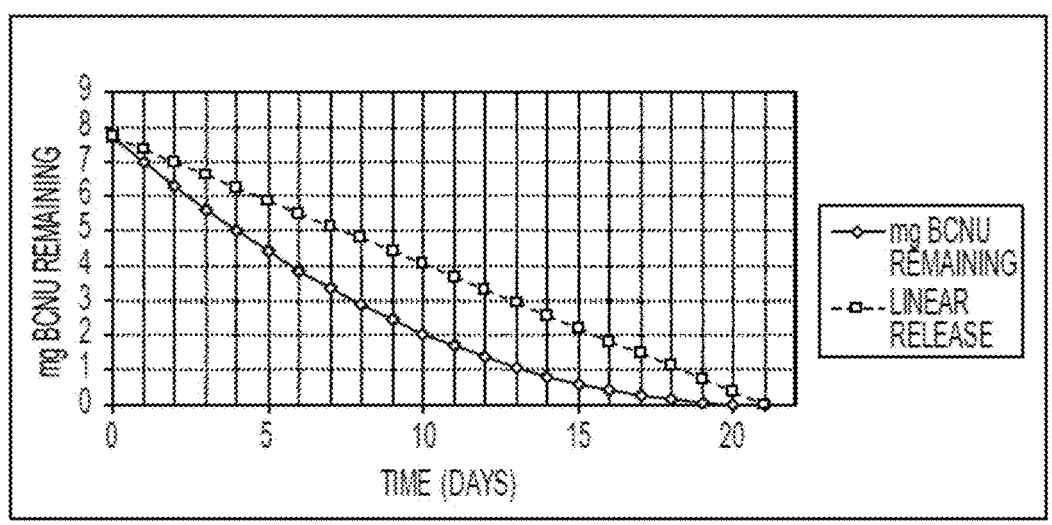
FIG. 5(B) is a table containing the drug release characteristics given different initial lengths for the rod and strip geometry.
FIG. 6 provides a graphical representation of the degradation release model used to predict from a rod-shaped wafer having initial dimensions $l_o$=15 mm, $r_o$=0.5 mm.

Inspection of the models reveals that the critical dimensions in terms of controlling release time are $r_o$ for the rod and $d_o$ for the strip. Thus small adjustments in the other dimensions only slightly affect the shape of the release curve but not the release time. As shown by FIG. 5B, changing the initial length of the wafer seems to have little effect on their drug release characteristics. The ideal length for the rod and strip was determined to be 15 mm as this would be the expected average diameter tumors to be treated by this design. Having fixed the length, the radius of the rod, being its critical dimension, could then be calculated to provide a total release time of 21 days. This was determined to be 0.5 mm. In the case of the strip, both the width and thickness must still be determined after a length is decided upon. The maximum width safe for a trajectory was thought to be ~5 mm. The maximum allowable width is desirable because maximizing width allows the strip to approximate a slab geometry most closely. Having fixed its length and width, the critical dimension thickness can be calculated to provide the correct release time. This was determined to be 1 mm. FIG. 6 graphically illustrates the degradation release model used to predict from a rod-shaped wafer having initial dimensions $l_o$=15 mm, $r_o$=0.5 mm. A line showing perfectly linear release of the entire mass of drug over 21 days is provided for comparison. It is evident that such a model predicts a significant deviation from linear release ($R^2$=0.6508).

Figure 7:
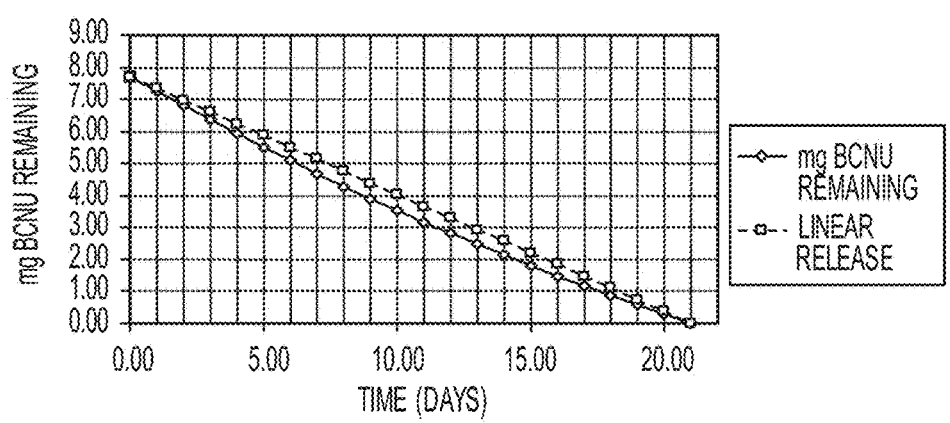
FIG. 7 provides a graphical representation of the degradation release model used to predict release from a strip shaped wafer having initial dimensions $l_o=15$ mm, $w_o=5$ mm, $d_o=1$ mm.
Figure 8A:
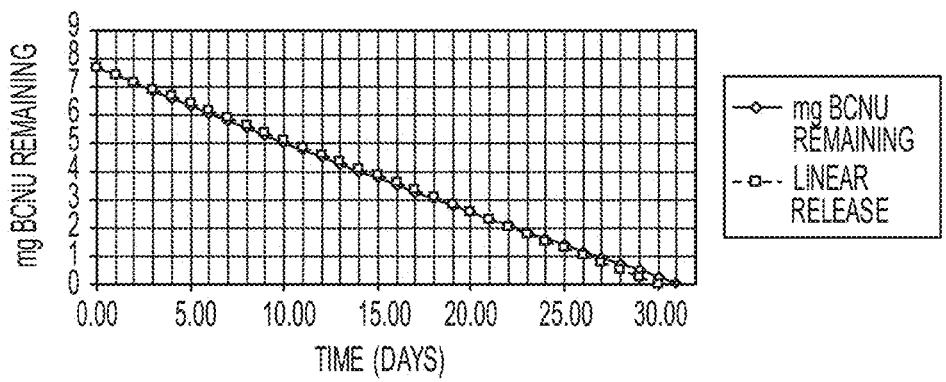
FIGS. 8(A)-(C) provide graphical representations of the expected release curves using updated degradation model for various geometries.
Figure 8B:
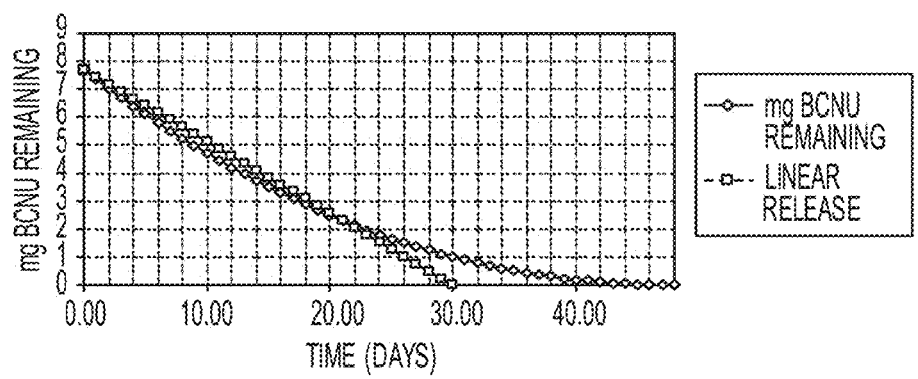
Figure 8C:
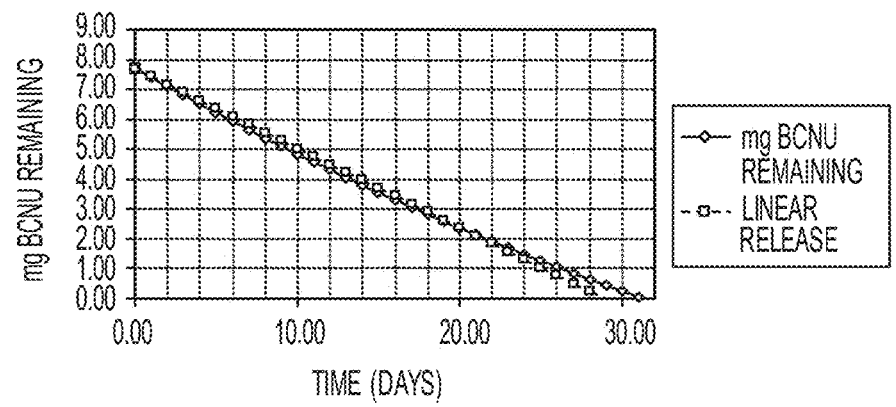

It thus appears that a rod geometry while offering advantages of cost and convenience would be expected to deviate significantly from the release pattern of Gliadel®. The strip geometry does successfully avoid this problem as was its purpose. FIG. 7 graphically illustrates the degradation release model used to predict release from a strip shaped wafer having initial dimensions $l_o$=15 mm, $w_o$=5 mm, $d_o$=1 mm. A line showing perfectly linear release of the entire mass of drug over 21 days is provided for comparison. It is evident that such a model predicts a very linear release for this geometry ($R^2$=0.9765). However, further research into the release characteristics of Gliadel® revealed that only about 70% of the wafer has usually degraded in 3 weeks [5]. Also, close inspection of the expected release curve shows that the release of the last 1 mg of drug is responsible for nearly ⅓ of the total release time. Thus the model needed to be recalibrated. The value of v was adjusted so that only 70% of a Gliadel® wafer is expected to degrade in 3 weeks. Similarly, the critical dimensions of the other geometries were also adjusted so that for the given value of v, only 70% of the initial volume was expected to degrade over 3 weeks. Thus by focusing only on the first 70% of release, the release curves of FIG. 8 can be obtained. FIGS. 8(A)-(C) shows the expected release curves using updated degradation model for various geometries. A line showing linear release of 70% of the drug over 21 days is also shown. FIG. 8(A) demonstrates the Gliadel® wafer whereby $R^2$ through first 70% of release (21 days)=0.9973. FIG. 8(B) demonstrates rod shaped wafer having initial dimensions $l_o$=15 mm, $r_o$=0.5 mm. $R^2$ through first 70% of release (21 days)=0.9661. FIG. 8(C) demonstrates strip shaped wafer having initial dimensions $l_o$=15 mm, $w_o$=5 mm, $d_o$=1 mm. $R^2$ through first 70% of release (21 days)=0.9931.

It is evident that when considering the first 70% of release, the rod geometry degrades in an adequately linear fashion and does not need to be replaced with the more cumbersome strip geometry.

Figure 9:
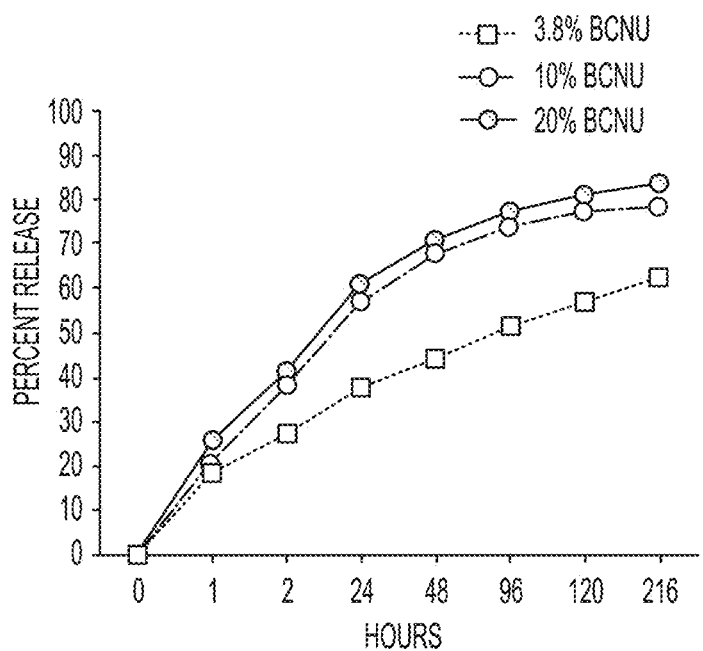
FIG. 9 provides a graphical representation of the drug release from 14 mm diameter, 1 mm thick disks with varying percent weight loading.

Actual data regarding the release of BCNU from pCPP-SA over time is not readily available. However, the data in FIG. 9 raises some important questions which may influence the choice of a model. FIG. 9 graphically shows the drug release from 14 mm diameter, 1 mm thick disks with varying percent weight loading. As shown, the 3.8% loaded disk is essentially equivalent to a Gliadel® wafer [1]. The shape of the curves do not indicate a zero order release as would be expected if surface degradation were the only mechanism controlling release. The fact that there are distinct curves for differing weight percentages belies a dependence on initial concentration which would not be predicted by a simple degradation controlled model. Finally, the drug release appears to occur much faster than over the three week period required for degradation of the wafer. These discrepancies indicate that drug release may be controlled by other mechanisms in addition to surface degradation of the polymer.

Modeling drug release in such a case can be made arbitrarily complex and any subset from a myriad of mechanisms can be modeled. For the purposes of this design, a simple model which shows the correct trends and correct relative shapes of the curves will be used to estimate the necessary size of the wafer rod. Because many basic properties such as the solubility of BCNU in pCPP-SA are not readily available, the model must be based upon simple parameters which are known or can easily be obtained by fitting to experimental data.

Figure 10:
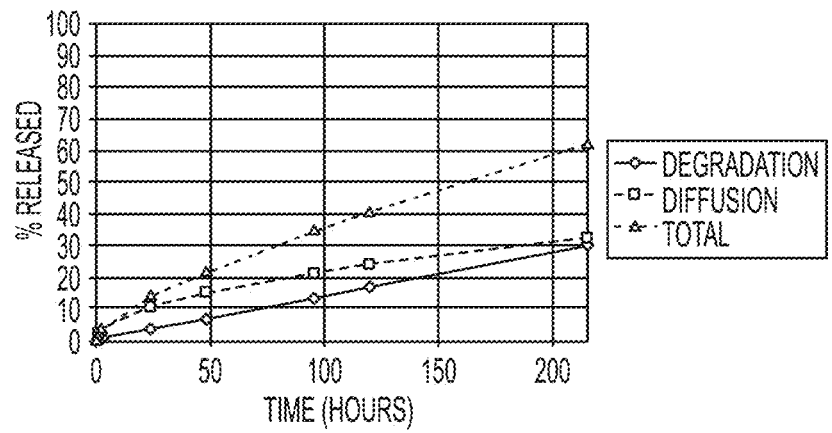
FIG. 10 provides a graphical representation of the predicted release from Gliadel® wafer using combined diffusion and degradation model.

The Higuchi equation was selected to model the diffusion component of the total drug release. By making the assumption that the concentration gradient outwards from the surface of the wafer is linear, the equation is simplified. In the case of a slab geometry (diffusion only from the two primary faces), the equation reduces to:

$$M_{(t)} = A\sqrt{2DtC_sC_o} \text{ for } C_o >> C_s \quad (6)$$

Where $M_{(t)}$ is the mass of drug released at time t, A is the total area of both faces of the slab, D is the diffusivity of the drug in the surrounding medium, $C_s$ is the solubility of the drug in the polymer matrix, and $C_o$ is the initial concentration of the drug [8]. A combined model was formed which summed the release due to degradation as in the previous model with release due to diffusion as predicted by the Higuchi equation. This model was then first applied to predict the release from disk shaped wafers. FIG. 10 graphically illustrates the predicted release from Gliadel® wafer using combined diffusion and degradation model. The contribution of each of the mechanisms is shown. The value of v was again adjusted, this time to reflect the necessary simplification that all degradation and diffusion occurred on the primary face surfaces of the wafer and that 70% of such degradation occurred in 21 days. Because values of D and $C_s$ were not readily available, they were combined into one term, $DC_s$ and its value was calculated such that the total percent release value predicted for 216 hours would match the observed value from FIG. 9.

Figure 11:
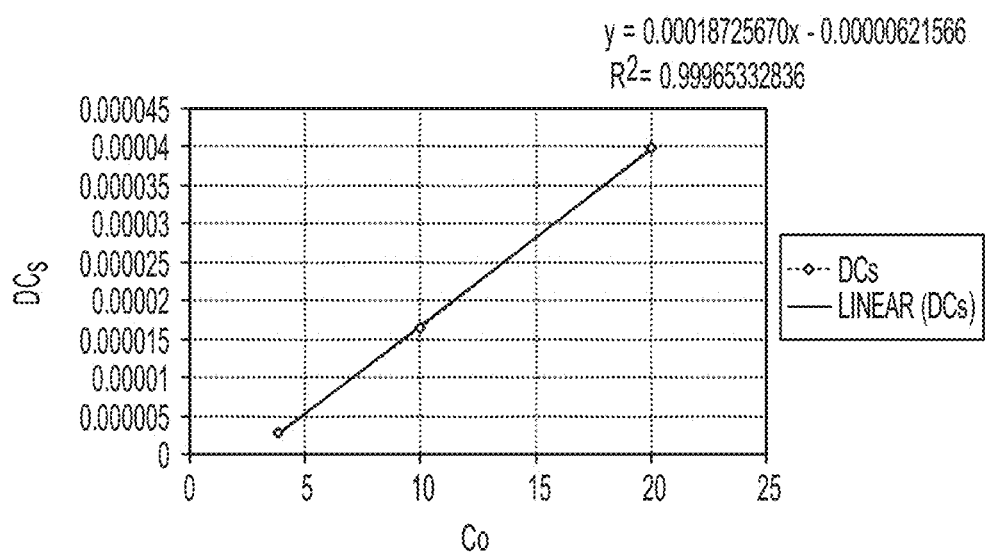
FIG. 11 provides a graphical representation of the computed $DC_s$ values plotted against the initial concentrations of their wafers.

The model must then be applied to predict the release from a rod geometry. However, unlike FIG. 9 which was available for disk geometry, no experimental data is available for a rod geometry. Thus the release profiles for rod shaped wafers of different initial concentrations or loading are unknown. Thus $DC_s$ values which were calculated for each of the wafers in FIG. 9 by fitting to the available experimental data, cannot immediately be calculated for rod shaped wafers by the same process. However, when the computed $DC_s$ values of each of the wafers were plotted against the initial concentrations of those wafers, as shown in FIG. 11, a clear linear relationship was observed. In FIG. 11, the computed $DC_s$ values are plotted against the initial concentrations of their wafers. An excellent regression correlation is observed and the function is used to calculate values of DCs in other geometries based on their initial concentrations. This allowed $DC_s$ values to be interpolated as a function of initial concentration. Furthermore, the Higuchi equation for cylinders does not simplify as it did in the case of slab geometry:

$$\left(1 - \frac{M_t}{M_o}\right)\ln\left(1 - \frac{M_t}{M_o}\right) + \frac{M_t}{M_o} = \frac{4DC_s t}{C_o r_o^2}. \quad (7)$$

$M_o$ is the initial mass of drug loaded into the polymer [8].

Figure 12:
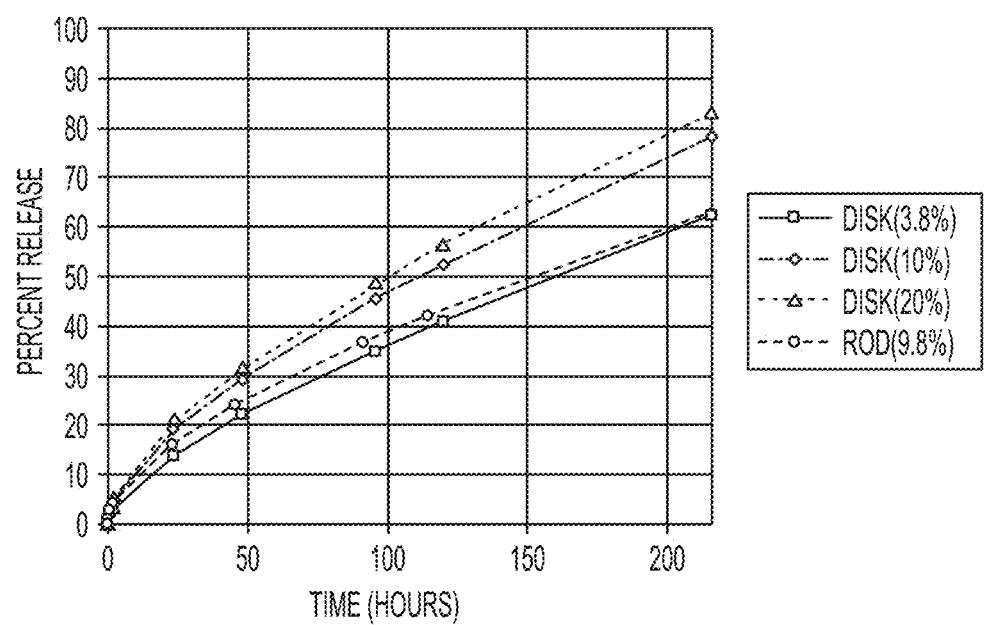
FIG. 12 provides a graphical representation of the predicted release curves for disk shaped wafers with weight loadings of 3.8%, 10%, and 20%.

Thus, it must be numerically solved to obtain the appropriate radius to give the proper release profile. A radius of 1.165 mm yields the appropriate value at 216 hours to match the value given in FIG. 9 for the Gliadel® wafer equivalent. FIG. 12 graphically illustrates the predicted release curves for disks shaped wafers with weight loadings of 3.8%, 10%, and 20%. Also plotted is the expected release from the proposed rod geometry with $l_o$=15 mm and $r_o$=1.17 mm which when loaded with the same amount of drug as a Gliadel® wafer has a 9.8% weight loading. The release curve of the proposed geometry closely follows the Gliadel® equivalent 3.8% weight loaded disk shaped wafer.

Figure 13:
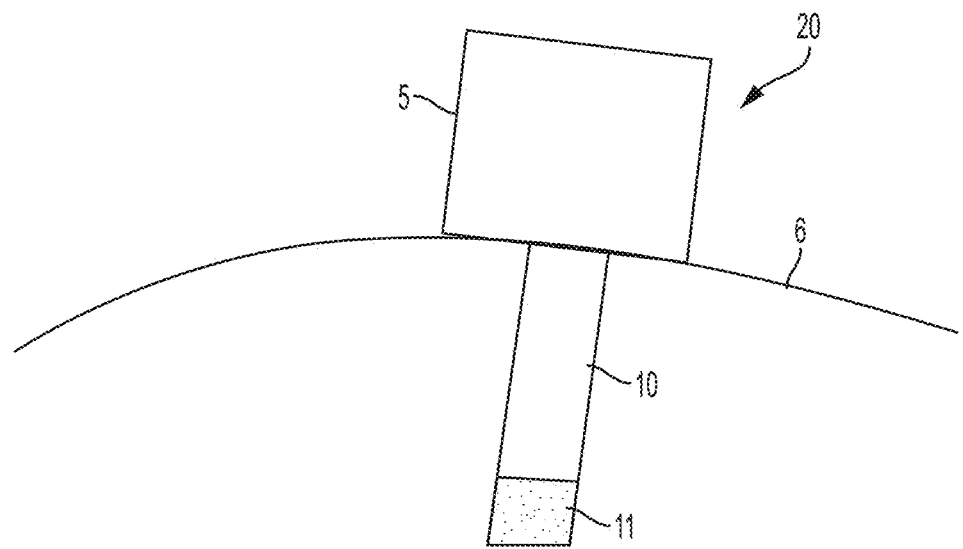
FIG. 13 is a schematic side view of the basic embodiment of the claimed invention, comprising the insertion device and an interface member on top of the skull.
Figure 14:
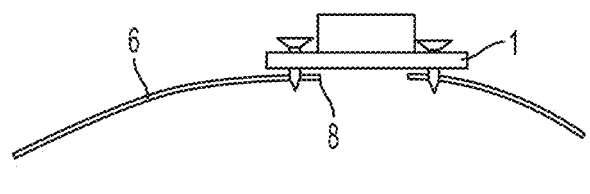
FIG. 14 is a schematic side view of the mount on the skull
Figure 14:
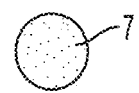
Figure 15:
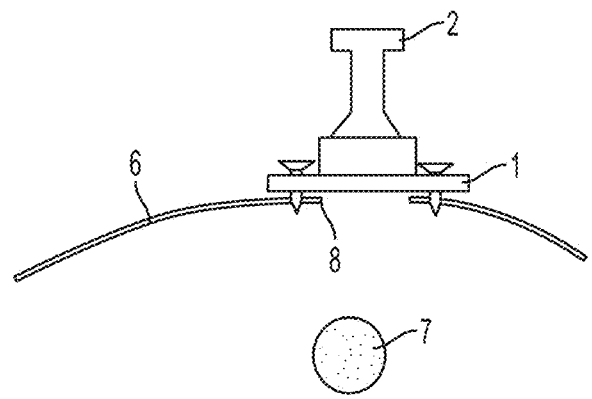
FIG. 15 is a schematic side view of the mount and trajectory guide.
Figure 16:
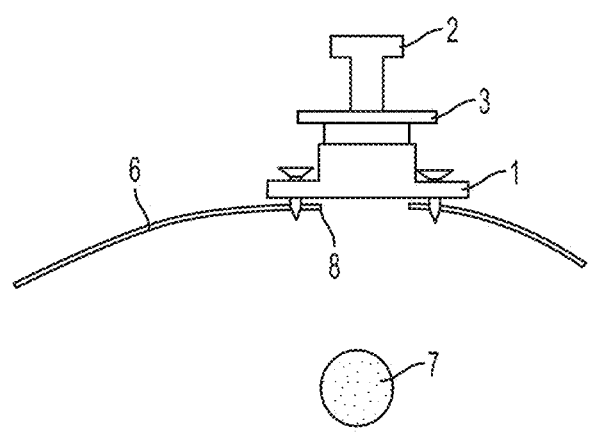
FIG. 16 is a schematic side view of the trajectory guide clamped to the mount via the trajectory clamp.
Figure 17:
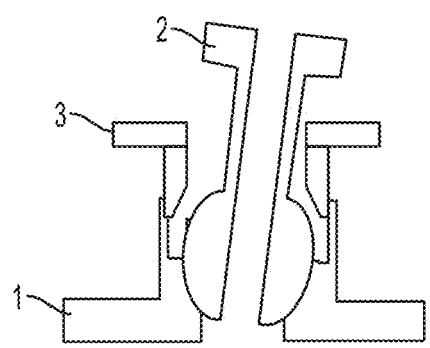
FIG. 17 is a schematic side view of the trajectory clamp unlocked.
Figure 18:
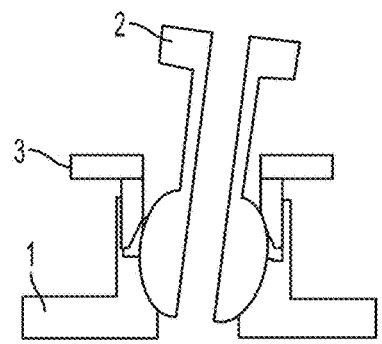
FIG. 18 is a schematic side view of trajectory clamp locking the trajectory guide into place.
Figure 19:
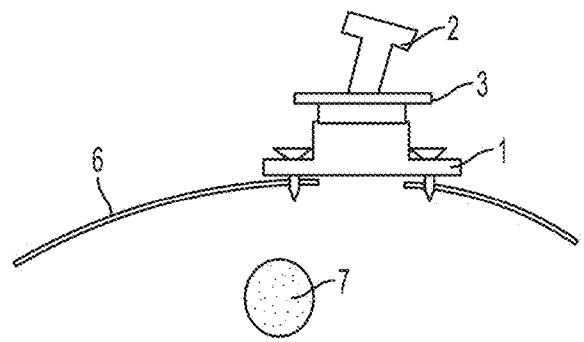
FIG. 19 is a schematic side view of the trajectory guide locked into position on the mount via the trajectory clamp.

Turning now to the drawings, FIG. 13 illustrates an exemplary system 20 for intracranial delivery of a diagnostic or therapeutic solid agent 11 (or other materials devices or other materials or devices in addition thereto) to the brain of a subject comprising an insertion device 10 and an interface member 5 disposed or in communication with the skull. The insertion device 10 may be adapted to retain and release the diagnostic or therapeutic solid agent 11 (or other materials or devices) for delivery to the brain. The interface member 5 may be adapted to accommodate the insertion device 10. The interface member 5 may incorporate a means, device or system to align the insertion device 10 to a predetermined trajectory and/or location in the brain. The interface member 5 may also incorporate a means, device or system for locking or stabilizing the insertion device 10 to a predetermined position or trajectory in the brain. The interface member 5 may also incorporate a navigation system for tracking the position of the insertion device 10. The biodegradation rate of the diagnostic or therapeutic solid agent 11 may be optimized to insure desired dosage over time for the patient. Although not shown in the instant drawings, the insertion device 10 may, for example, be comprised of a sleeve 12 and an obturator 14. The obturator 14 may be sized to fit the sleeve 12. The geometry of the diagnostic or therapeutic solid agent 11 (materials or device) may be commensurate, compatible, or attachable with the dimensions or structure of the insertion device 10. The system 20 may also deliver additional agents, materials or devices. The system 20 may incorporate a catheter for the delivery of additional agents, materials or devices. The system 20 may also allow for any or all parts, materials or components of or affiliated with the agent delivery process to be monitored by a radiological imaging means, such as a magnetic resonance imager, a CT scanner, a fluoroscope, a bi-planar fluoroscope, a PET scanner, a nuclear medicine camera, or any other such biomedical imaging device (not shown). The system 20 may also be used to withdraw unused portions of the diagnostic or therapeutic solid agent 11 (materials or devices) from the brain. The system 20 may be used to withdraw materials other than the diagnostic or therapeutic solid agent 11 from the brain. The system 20 may incorporate a diagnostic or therapeutic solid agent co-formulated with another diagnostic or therapeutic agent, such as an MR contrast enhancing agent. The diagnostic or therapeutic solid agent may be a carmustine material. The item being delivered may be any anti-tumoral agent, or any other material as desired or required for a give application or procedure. The system 20 may be adapted for other delivery applications to the brain such as deep brain electrodes or other sustained release devices It should be appreciated that the various embodiments of the present invention diagnostic and/or therapeutic system and related method thereof are not necessarily limited to the brain of a subject. It may also be used in the organ structures or tubular structures, as well as portions and locations thereof. An organ includes, for example, a solid organ, a hollow organ, parenchymal tissue (e.g., stomach, brain, esophagus, colon, rectum, kidneys, liver, etc.) and/or stromal tissue. Hollow organ structures includes, for example, stomach, esophagus, colon, rectum, and ducts, or the like. A tubular structure may include a blood vessel. A blood vessel may include one or more of the following: vein, venule, artery, arterial, or capillary.

Further, various embodiments of the present invention method and system may be directed to or communicated with one or more locations of the subject, such as, but not limited to one or more locations of the organ, tubular structure, etc.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware.

Moreover, it should be appreciated that any of the components or modules referred to with regards to any of the present invention embodiments discussed herein, may be a variety of materials and/or composites as necessary or required.

Still further, it should be appreciated that any of the components or modules (or combination thereof) may provide shape, size and volume contoured by adjusting its geometry and flexibility/rigidity according to the target location or anatomy (or region, including structure and morphology of any location) being treated.

FIGS. 14-31 illustrate one embodiment of the invention. FIGS. 14-19 display one embodiment of a mount that comprises a mount 1, trajectory guide 2, and mount clamp 3. The procedure for the use of these parts may be, for example and not limited thereto, as follows: 1) a small burr hole 8 is created in the skull 6; 2) the mount 1 is screwed to the skull to prevent movement; 3) the trajectory guide 2 is inserted; 4) the trajectory guide 2 is adjusted to the desired trajectory angle and the mount clamp 3 is twisted to secure the angle. It should be appreciated that different clamping solutions can be employed to secure the proper angle of the trajectory guide or proper components of the system and working piece (i.e., agent material). Such clamping solutions may include, but not limited thereto, Tuey-Borst fitting, modified Tuey-Borst fitting, or other available or modified clamping systems.

Figure 20:
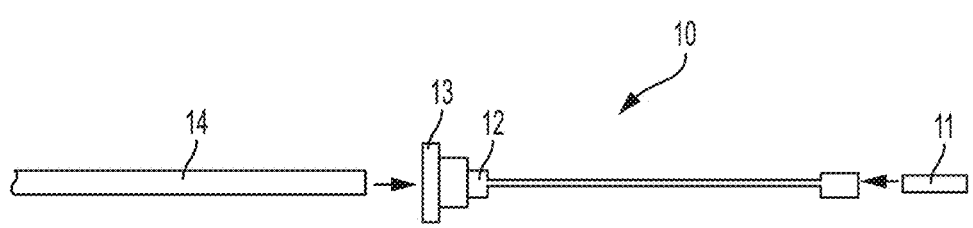
FIG. 20 is a schematic side view of the insertion device component parts comprising the obturator, sleeve clamp, sleeve, and therapeutic or diagnostic agent.
Figure 21A:
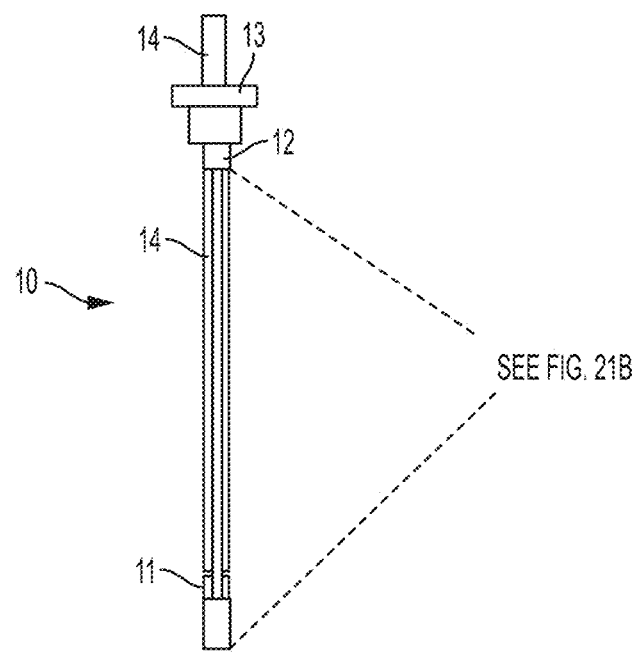
FIG. 21(A) is a schematic side view of the assembled insertion device comprising the obturator, sleeve clamp, sleeve, and therapeutic or diagnostic agent.
Figure 21B:
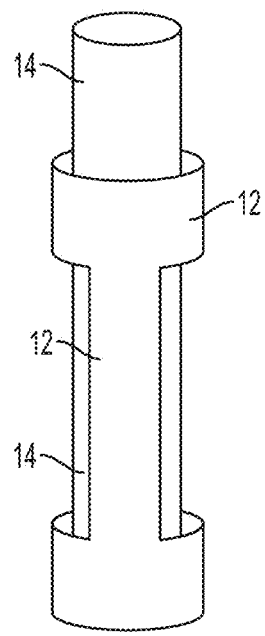
FIG. 21(B) is an enlarged schematic partial view of the obturator shown in FIG. 21(A).
Figure 22:
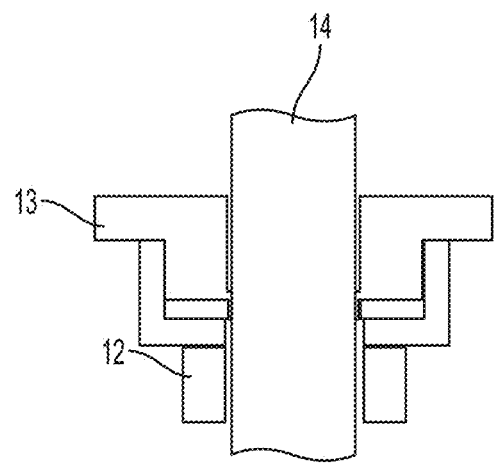
FIG. 22 is a schematic view of the sleeve clamp locking the obturator to the sleeve.

FIGS. 20-22 depict one embodiment of the insertion device, comprising an obturator 14, a sleeve clamp 13, a sleeve 12, and a solid therapeutic or diagnostic agent 11. The solid therapeutic or diagnostic agent 11 and obturator 14 are front-loaded into a sleeve 12, as shown in FIG. 20. The sleeve 12 may be a needle having two long "windows" cut therein along its length to provide lateral access to the interior of the needle. The sleeve 12 should have the proper inner diameter to accommodate the solid therapeutic or diagnostic agent 11 and may be approximately 18 cm long (or adjusted as required or desired) in order to traverse the longest expected trajectories to the deepest parts of the brain safely accessed by stereotaxis. The agent may be accommodated inside the sleeve, or outside as well or combination thereof. In an approach, the sleeve 12 may be machined in a way that exerts enough frictional force on the sides or any portion or location of the solid therapeutic or diagnostic agent to resist the force of gravity and otherwise hold the solid therapeutic or diagnostic agent in place within the insertion device. It should be appreciated that other desired or required retention means may be implemented. The sleeve 12 may also be outfitted with fiducial markers (not shown) that would make it visible to the image guidance system in order to monitor its depth when it is inserted into the brain. It should be appreciated that there are other ways using other available systems, which include making the therapeutic or diagnostic agent it self somehow visible (perhaps by incorporating a contrast agent in the therapeutic or diagnostic agent) or outfitting the sleeve apparatus with an LED or a coil at the tip. The obturator 14 is essentially a stiff rod having the same diameter as the wafer. Its length may be approximately 24 cm. It should be appreciated that any length or size may be implemented as desired or required for the procedure. The sleeve clamp 13 can be a standard Tuey-Borst fitting which, when tightened, couples the sleeve to the obturator. Other clamping solutions can also be used. When twisted, the sleeve clamp 13 applies pressure to a flexible material inside causing the material to expand and therefore decrease the size of the bore going through it. Reduction in the bore diameter causes it to tighten around the obturator 14 going through it and thus couples the obturator to the sleeve clamp 13 and attached sleeve 12, as shown in FIG. 22. When the obturator 14, sleeve clamp 13, sleeve 12, and solid therapeutic or diagnostic agent 11 are assembled accordingly, the resulting assembly is an insertion device 10, as shown in FIGS. 21(A)-(B). FIG. 21(B) is an enlarged partial view of FIG. 21(A).

Figure 23:
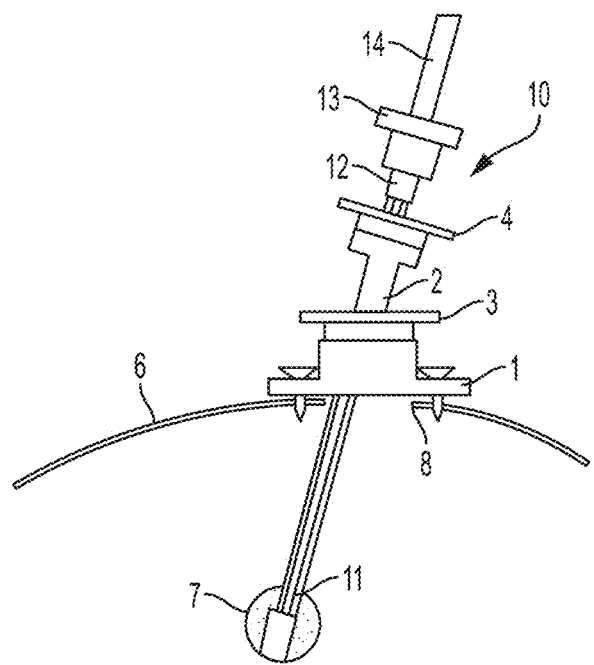
FIG. 23 is a schematic side view of an apparatus comprising mount, trajectory guide, and insertion device.
Figure 24:
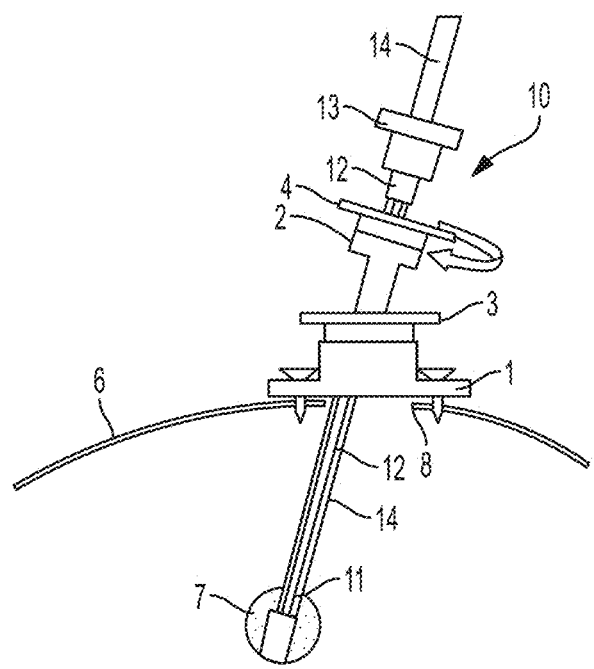
FIG. 24 is a schematic side view of the obturator part of the insertion device being locked to trajectory guide.

The insertion device 10 may then be inserted into the brain through the trajectory guide 2 and mount 1. The entire apparatus is shown in FIG. 23 for an exemplary approach. The trajectory clamp 4 is then twisted to lock the insertion device 10 at the proper depth, as shown in FIG. 24. It should be appreciated that different clamping solutions can be employed to secure the proper depth of the insertion device 10.

Figure 25:
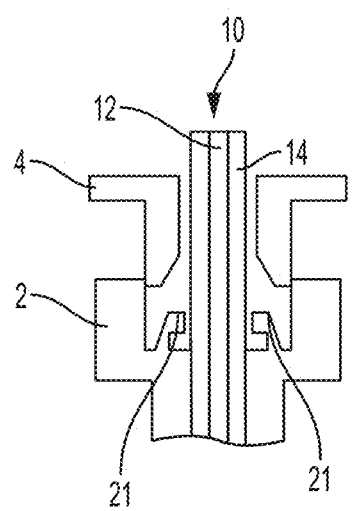
FIG. 25 is a schematic side view of the insertion device unlocked to the trajectory guide.
Figure 26:
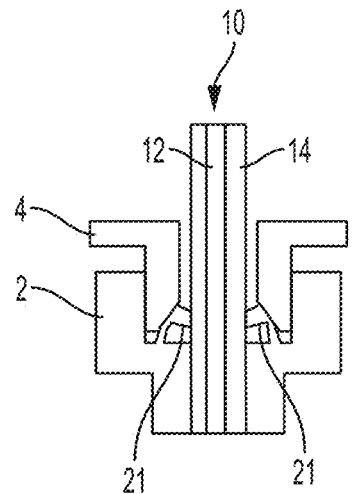
FIG. 26 is a schematic side view of the insertion device locked to the trajectory guide.

The trajectory guide 2 may be modified to add a second locking mechanism, to include arms 21 for example, as shown in FIG. 25. As the trajectory clamp 4 is tightened, the trajectory clamp 4 moves down the threaded walls of the modified end of the trajectory guide 4. The force applied forces the two docking or clamp arms 21 together, causing them to grip and hold the obturator 14 while leaving the outer sleeve 12 unhindered as shown in FIG. 26. The radial orientation of the insertion device 10 may be adjustable in such a way that ensures the "windows" on the sleeve 12 always align with the arms 21 of the trajectory guide clamp.

Figure 27:
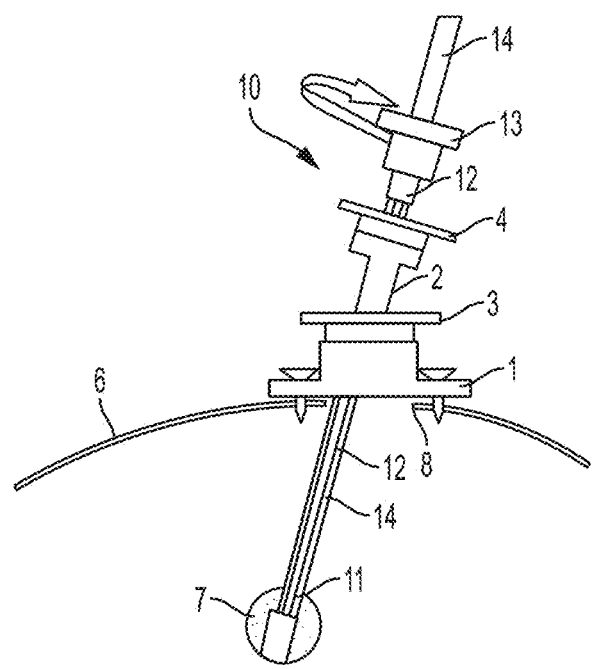
FIG. 27 is a schematic side view of the sleeve clamp being loosened, unlocking the obturator from the sleeve.
Figure 28:
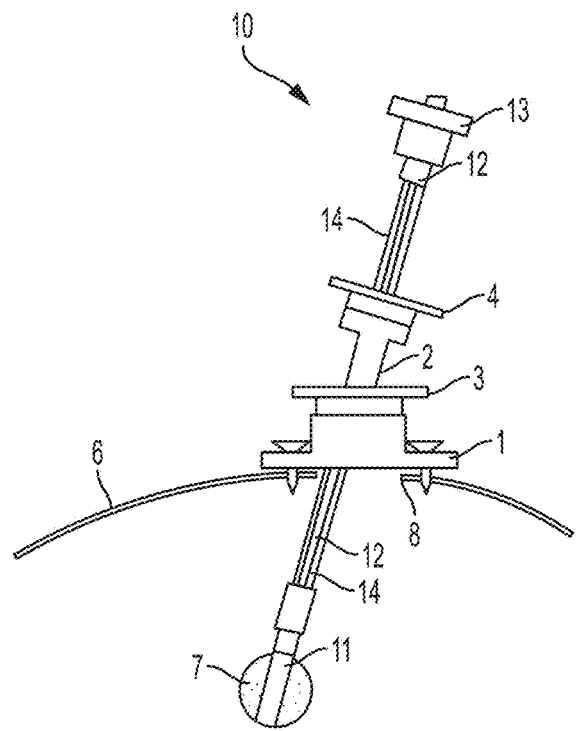
FIG. 28 is a schematic side view of the sleeve lifted, leaving therapeutic or diagnostic agent in place in the brain.
Figure 29:
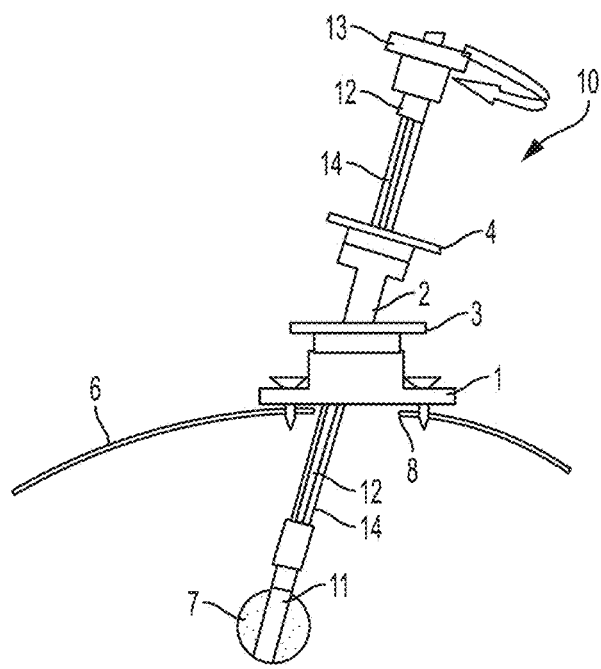
FIG. 29 is a schematic side view of the sleeve clamp being tightened, locking the obturator to the sleeve.
Figure 30:
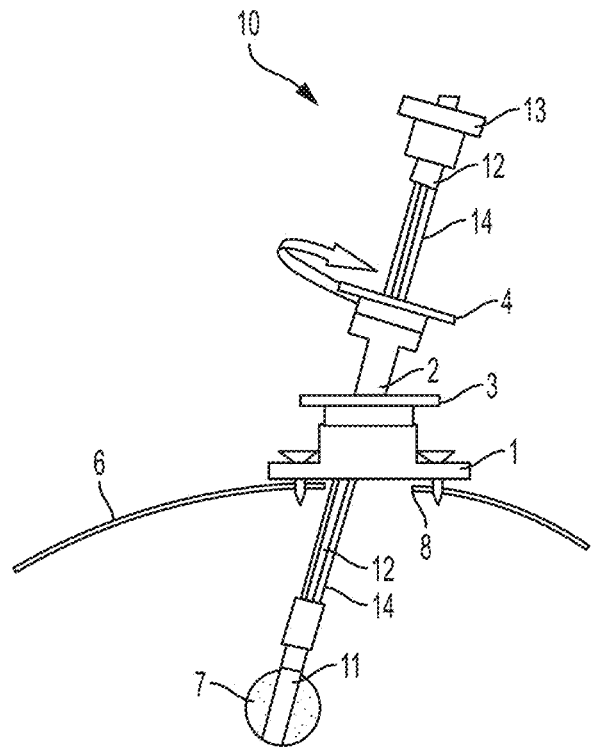
FIG. 30 is a schematic side view of the trajectory clamp being loosened, unlocking the insertion device from the trajectory guide.
Figure 31:
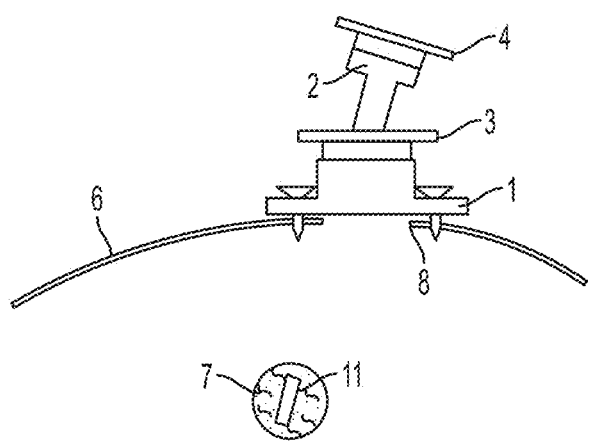
FIG. 31 is a schematic side view of the trajectory guide and mount after the insertion device is withdrawn, leaving therapeutic or diagnostic agent in place in the brain.

The sleeve clamp 13 may then be loosened to disengage the sleeve 12 from the obturator 14, as shown in FIG. 27. The sleeve 12 may then be slid back, while the obturator 14 remains fixed to the trajectory guide 2, and thus holds the solid therapeutic or diagnostic agent 11 in place preventing it from sliding back with the sleeve 12, as shown in FIG. 28 The sleeve clamp 13 may then be retightened to couple the sleeve 12 and obturator 14, as shown in FIG. 29. The trajectory clamp 4 may then be loosened to release the obturator 18, as shown in FIG. 30. The entire insertion device 10 may then be removed from the brain leaving behind the solid therapeutic or diagnostic agent 11 in place at the site of the tumor 7, as shown in FIG. 31.

The entire design may be disposable for maximum safety or sterlizable for reuse, as well as any combination thereof. New parts may be constructed from plastics but the actual modified needle or sleeve may be stainless steel. It should be appreciated that the subject invention can be made of any material that gives adequate performance in terms of rigidity, sterilizability, and visibility to the image guidance system.

It should also be appreciated that the subject invention can be used to deliver additional agents. Furthermore, it should be appreciated that a catheter may be introduced into the brain for the delivery of additional agents. It should also be appreciated that any or all parts of the agent delivery process can be monitored by a radiological imaging means, such as a magnetic resonance imager, a CT scanner, a fluoroscope, a bi-planar fluoroscope, a PET scanner, a nuclear medicine camera, or any other such biomedical imaging device. It should also be appreciated that the subject invention could accommodate newer systems including RF instead of IR and actual intra-operative MRI/CT.

It should also be appreciated that the insertion device may be used as a means for withdrawing unused portions of the diagnostic or therapeutic solid agent from the brain. Moreover, it should be appreciated that the insertion device may be used to withdraw materials other than the diagnostic or therapeutic solid agents from the brain. It should also be appreciated that the diagnostic or therapeutic solid agent may be co-formulated with another diagnostic or therapeutic agent, such as an MR contrast enhancing agent. The diagnostic or therapeutic solid agent may be a carmustine material or other anti-tumoral agents or materials. It should be appreciated that the interface member 5 as discussed in FIG. 13 may be affected by a variety of clamping, aligning, mounting, retaining, releasing, and/or locking devices and methods. For instance, referring to FIGS. 14-31, a variety components and methods were disclosed but are presented for illustration only and should not be construed as limiting the various embodiments of the invention in any way.

EXPERIMENTAL RESULTS

Practice of the invention will be still more fully understood from the following examples and experiments, which are presented herein for illustration only and should not be construed as limiting the invention in any way.

The time scale in FIG. 9 reveals that the wafers actually undergo a very rapid release within the first few hours. Even the data itself from FIG. 9 is for in vitro release, which may deviate significantly from in vivo release [9].

Changes in geometry were examined in this study. However, for a given geometry, many other variables may be controlled in order to manipulate the release profile. Changing the ratio of monomers in pCPP-SA from 20:80 to other values can give degradation times ranging anywhere from 1 day to 3 years [2]. The crystallinity of the wafers may be influenced by the method used to produce them such as compression molding or melt casting. This too has an effect on the release characteristics. The 9.8% weight loading proposed by the design falls well short of the maximum loading of about 32% at which point the loading begins to affect structural characteristics of the wafer [10]. Thus even if the final model does not prove to be completely accurate, adjustment of dimensions and other control variables should allow for the formulation of a suitable rod shaped wafer The necessary geometry of the carmustine wafer is determined to be a rod of length 15 mm and radius 1.17 mm. These dimensions are well within the acceptable range for instruments that enter the brain. Neuroendoscopes may have diameters of more than 4 mm [7]. In addition, because the length does not greatly affect the release pattern, the carmustine wafer could be packaged as a single 120 mm rod corresponding to the maximum Gliadel® wafer dosage of 8 wafers. The surgeon would then have the option to break the rod into pieces of variable length to suit coverage of the entire tumor.

The system chosen for the stereotactic trajectory guide for this experiment was the Navigus® by Image Guided Neurologics (IGN).

It should be appreciated that the sizes, shapes, contours, lengths, and widths of any components or material discussed herein may be adjusted or altered as required or desired for clinical or procedural uses.

The delivery device would thus remain valid even if dimensions must be adjusted slightly. Furthermore, the device could be used to deliver not only BCNU wafers to tumors but could be applied to many other delivery applications to the brain such as deep brain electrodes or other sustained release devices besides BCNU wafers.

REFERENCES CITED

The following patents, applications and publications as listed below and throughout this document are hereby incorporated by reference in their entirety herein. The composition, devices, systems and methods of various embodiments of the invention disclosed herein may utilize aspects disclosed in the following U.S. Patents, foreign patents, and publications and are hereby incorporated by reference herein in their entirety.

U.S. Patent Documents

| 6,902,569 | June 2005 | Parmer et al | 606/108 |
| 6,752,812 | June 2004 | Truwit | 606/130 |
| 5,776,144 | July 1998 | Leysieffer et al | 606/130 |
| 5,643,286 | July 1997 | Warner et al | 606/130 |
| 4,789,724 | December 1988 | Domb et al | 528/176 |
| 4,757,128 | July 1988 | Domb et al | 528/271 |

Foreign Patent Documents

| 29612100 | September 1996 | DE | A61B/1/018 |
| 0427358 | May 1991 | EP | A61B/6/00 |

Other Publications

1. P. Sampath, H. Brem, Implantable Slow-Release Chemotherapeutic Polymers for the Treatment of Malignant Brain Tumors, Cancer Control Journal. 5 (1998).

2. M. S. Lesniak, H. Brem, Targeted Therapy for Brain Tumours, Nature Reviews. 3 (2004) 499-508.

3. C. Guerin et al., Recent advances in brain tumor therapy: local intracerebral drug delivery by polymers, Investigational New Drugs. 22 (2004) 27-37.

4. S. Maciej et al., Drug Delivery to Tumors of the Central Nervous System, Current Neurology and Neuroscience Reports 1 (2001) 210-216.

5. Gliadel® Wafer package insert, MGI Pharma Inc.

6. P. Wang, J. Frazier, H. Brem, Local Drug Delivery to the Brain, Advanced Drug Delivery Reviews 54 (2002) 987-1013.

7. T. Taira et al., 3-D Neuroendoscope and CM-cube system in neurosurgery, Clinical Neurology and Neurosurgery 99 (1997) 4040.

8. R. Baker, Controlled Release of Biologically Active Agents. 1987 50-73.

9. A. Gopferich, J. Tessmar, Polyanhydride degradation and erosion. Advanced Drug Delivery Reviews 54 (2002) 911-931.

10. E. Sipos et al., Optimizing interstitial delivery of BCNU from controlled release polymers for the treatment of brain tumors, Cancer Chemother Pharmacol 39 (1997) 383-389.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A system for intracranial delivery of a diagnostic or therapeutic solid agent to the brain of a subject, said system comprising:

an insertion device for delivery of the diagnostic or therapeutic solid agent to the brain, said insertion device being configured to retain the diagnostic or therapeutic solid agent to the insertion device and to release the diagnostic or therapeutic solid agent from the insertion device; and an interface member configured to be attached to the subject's skull, said interface member being further configured to hold said insertion device at a predetermined alignment angle with respect to the subject's skull, wherein said insertion device comprises a sleeve configured to hold the diagnostic or therapeutic solid agent, an obturator sized to fit in said sleeve, and a first locking mechanism configured to releasably couple said sleeve and said obturator to move together as an assembly, wherein said interface member comprises a second locking mechanism configured to secure said obturator from moving relative to said interface member while allowing said sleeve to be withdrawn relative to said obturator, and the diagnostic or therapeutic solid agent has an outer diameter substantially corresponding to an inner diameter of the sleeve.

2. The system of claim 1, wherein said sleeve is configured to hold the diagnostic or therapeutic solid agent in the sleeve by a frictional force.

3. The system of claim 1 wherein said interface member includes a mount configured to attach to the patient's skull, and a trajectory guide configured to receive said insertion device and to lock the insertion device at a desired angle with respect to the patients skull via a clamp, and the holding of said insertion device comprises alignment of said insertion device to a predetermined trajectory in the brain.

4. The system of claim 3, wherein the holding of said insertion device comprises locking said insertion device to a predetermined position in the brain.

5. The system of claim 4, wherein said interface member comprises a navigation system for tracking a position of said insertion device.

6. The system of claim 1, wherein the holding of said insertion device comprises locking said insertion device to a predetermined position in the brain.

7. The system of claim 1, wherein said interface member comprises a navigation system for tracking a position of said insertion device.

8. The system of claim 1, wherein said interface member comprises a capture mechanism for retaining said insertion device for removal from the brain while insuring that the diagnostic or therapeutic solid agent remains placed within the brain.

9. The system of claim 1, further comprising the diagnostic or therapeutic solid agent detachably connected to said insertion device.

10. The system of claim 9, wherein said diagnostic or therapeutic solid agent has a biodegradation rate optimized to insure desired dosage over time for the subject.

11. The system of claim 1, wherein additional agents can be delivered.

12. The system of claim 1, further comprising a catheter configured to be introduced into the brain for delivery of additional agents.

13. The system of claim 1, further comprising an imaging system.

14. The system of claim 13, wherein said imaging system comprises at least one of a magnetic resonance imager, a CT scanner, a fluoroscope, a bi-planar fluoroscope, a PET scanner, and a nuclear medicine camera.

15. The system of claim 14, wherein said imaging system is configured for monitoring a location of the insertion device during intracranial delivery of the diagnostic or therapeutic solid agent to the brain of the subject.

16. The system of claim 1, wherein the insertion device is adapted for withdrawing unused portions of the diagnostic or therapeutic solid agent from the brain.

17. The system of claim 1, wherein the insertion device is adapted for withdrawing materials other than the diagnostic or therapeutic solid agent from the brain.

18. The system of claim 1, wherein the diagnostic or therapeutic solid agent is co-formulated with another diagnostic or therapeutic agent.

19. The system of claim 1, wherein the diagnostic or therapeutic solid agent is a carmustine material.

20. The system of claim 1, wherein said insertion device is adapted for other delivery applications to the brain including at least one of deep brain electrodes or a sustained release device.

21. A method for intracranial delivery of a diagnostic or therapeutic solid agent to the brain of a subject, said method comprising:
    detachably connecting the diagnostic or therapeutic solid agent to an insertion device via a friction fit at least partially within a sleeve of the insertion device for the delivery of the diagnostic or therapeutic solid agent to the subject;
    attaching a mount to the subject's skull;
    attaching the insertion device to the mount;
    aligning the insertion device to a predetermined trajectory relative to the brain of the subject;
    locking the insertion device at the predetermined trajectory via a clamp included in the mount;
    inserting the insertion device into the brain; and
    detaching the diagnostic or therapeutic solid agent from the insertion device in the brain of the subject,
    wherein detaching the diagnostic or therapeutic solid agent from the insertion device includes locking an obturator received at least partially in said sleeve so that the obturator cannot move relative to the mount, and withdrawing the sleeve relative to the obturator while the obturator remains locked relative to the mount.

22. The method of claim 21, further comprising locking said insertion device to a predetermined position in the brain.

23. The method of claim 21, further comprising navigating and tracking a position of said insertion device.

24. The method of claim 21, further comprising optimizing a biodegradation rate of the diagnostic or therapeutic solid agent to insure desired dosage over time for the subject.

25. The method of claim 21, wherein said delivery comprises retaining said insertion device for removal from the brain while insuring that the diagnostic or therapeutic solid agent remains placed within the brain.

26. The method of claim 21 wherein said delivery further comprises delivering additional agents to the brain.

27. The method of claim 21, further comprising inserting a catheter into the brain for delivering additional agents.

28. The method of claim 21 further comprising monitoring and/or imaging at least part of the insertion device during intracranial delivery of the diagnostic or therapeutic solid agent to the brain of the subject.

29. The method of claim 28 wherein said monitoring and/or imaging being provided by a radiological imaging system including at least one of a magnetic resonance imager, a CT scanner, a fluoroscope, a bi-planar fluoroscope, a PET scanner, and a nuclear medicine camera.

30. The method of claim 21, further comprising withdrawing unused portions of the diagnostic or therapeutic solid agent from the brain.

31. The method of claim 21, further comprising withdrawing materials other than the diagnostic or therapeutic solid agent from the brain.

32. The method of claim 21, further comprising co-formulating the diagnostic or therapeutic solid agent with another diagnostic or therapeutic agent.

33. The method of claim 21, wherein the diagnostic or therapeutic solid agent is a carmustine material.

34. The method of claim 21 wherein said delivery further comprises delivering applications to the brain including at least one of deep brain electrodes or a sustained release device.

35. A system for intracranial delivery of a diagnostic or therapeutic solid agent to one or more locations of a subject, said system comprising:
    an insertion device for delivery of the diagnostic or therapeutic solid agent to the one or more locations of the subject, said insertion device being configured to hold the diagnostic or therapeutic solid agent via a friction fit; and
    an interface member configured to be attached to the subject's cranium, said interface member being further configured to accommodate said insertion device at a predetermined alignment angle,
    wherein said insertion device comprises a sleeve configured to hold the diagnostic or therapeutic solid agent, an obturator sized to fit in said sleeve, and a first locking mechanism configured to releasably couple said sleeve and said obturator to move together as an assembly,
    wherein said interface member comprises a second locking mechanism configured to secure said obturator from moving relative to said interface member while allowing said sleeve to be withdrawn relative to said obturator.

36. The system of claim 35, wherein said insertion device is adapted to retain and release the diagnostic or therapeutic solid agent for delivery to the one or more locations of the subject.

37. The system of claim 36, wherein said obturator is sized to fit in said sleeve.

38. The system of claim 35, wherein the accommodation of said insertion device comprises locking said insertion device to a predetermined position in the one or more locations of the subject.

39. The system of claim 38, wherein said interface member comprises a navigation system configured for tracking the position of said insertion device.

40. The system of claim 35, wherein said interface member comprises a navigation system configured for tracking the position of said insertion device.

41. The system of claim 35, wherein said interface member comprises a capture mechanism for retaining said insertion device for removal from the one or more locations of the subject while insuring that the diagnostic or therapeutic solid agent remains placed within the one or more locations of the subject.

42. The system of claim 35, further comprising the diagnostic or therapeutic solid agent connected to said insertion device.

43. The system of claim 42, wherein said diagnostic or therapeutic solid agent has a biodegradation rate optimized to insure desired dosage over time for the subject.

44. The system of claim 35, wherein said sleeve is sized to hold the diagnostic or therapeutic solid agent by the friction fit.

45. The system of claim 35, wherein additional agents can be delivered.

46. The system of claim 35, further comprising a catheter configured to be introduced into the one or more locations of the subject for delivery of additional agents.

47. The system of claim 35 further comprising an imaging system.

48. The system of claim 47, wherein said imaging system comprises at least one of a magnetic resonance imager, a CT scanner, a fluoroscope, a bi-planar fluoroscope, a PET scanner, and a nuclear medicine camera.

49. The system of claim 48, wherein said imaging system is for monitoring at least part of the insertion device during intracranial delivery of the diagnostic or therapeutic solid agent to the brain of the subject.

50. The system of claim 35, wherein the insertion device is adapted for withdrawing unused portions of the diagnostic or therapeutic solid agent from the one or more locations of the subject.

51. The system of claim 35, wherein the insertion device is adapted for withdrawing materials other than the diagnostic or therapeutic solid agent from the one or more locations of the subject.

52. The system of claim 35, wherein the diagnostic or therapeutic solid agent is co-formulated with another diagnostic or therapeutic agent.

53. The system of claim 35, wherein the diagnostic or therapeutic solid agent is a carmustine material.

54. The system of claim 35, wherein said insertion device is adapted for other delivery applications to the one or more locations of the subject including at least one of electrodes or a sustained release device.

55. The system of claim 35, wherein the one or more locations of the subject comprises at least a portion of an organ.

56. The system of claim 35, where the one or more locations of the subject comprises at least a portion of a tubular structure.

57. The system of claim 56, wherein said tubular structure comprises a blood vessel.

58. A method for intracranial delivery of a diagnostic or therapeutic solid agent to one or more locations of a subject, said method comprising:
attaching the diagnostic or therapeutic solid agent to an insertion device for the delivery of the diagnostic or therapeutic solid agent to the subject;
mounting the insertion device to the subject;
aligning the insertion device to a predetermined trajectory relative to the one or more locations of the subject;
inserting the insertion device into the one or more locations of the subject; and
detaching the diagnostic or therapeutic solid agent from the insertion device in the one or more locations of the subject,
wherein, the insertion device comprises a sleeve that holds the diagnostic or therapeutic solid agent,
mounting the insertion device to the subject includes inserting the insertion device at least partly within an interface mechanism including a base that is secured to the exterior of the subject's skull, a guide that rotates at least partially with respect to the base, and a first locking mechanism that locks the guide at the predetermined trajectory with respect to the base, and
the diagnostic or therapeutic solid agent has an outer diameter that substantially corresponds to an inner diameter of the sleeve,
wherein detaching the diagnostic or therapeutic solid agent from the insertion device includes locking an obturator received at least partially in the sleeve via a second locking mechanism so that the obturator cannot move relative to the interface mechanism, and withdrawing the sleeve relative to the obturator while the obturator remains locked relative to the interface mechanism.

59. The method of claim 58, further comprising locking said insertion device to a predetermined position in the one or more locations of the subject.

60. The method of claim 58, further comprising navigating and tracking a position of said insertion device.

61. The method of claim 58, further comprising optimizing a biodegradation rate of the diagnostic or therapeutic solid agent to insure desired dosage over time for the subject.

62. The method of claim 58, wherein said delivery comprises retaining said device for removal from the one or more locations of the subject while insuring that the diagnostic or therapeutic solid agent remains in place within the one or more locations of the subject.

63. The method of claim 58 wherein said delivery further comprises delivering additional agents to the one or more locations of the subject.

64. The method of claim 58, further comprising inserting a catheter into the one or more locations of the subject for delivering additional agents.

65. The method of claim 58, further comprising monitoring and/or imaging at least a part of the insertion device during delivery of the diagnostic or therapeutic solid agent to the one or more locations of the subject.

66. The method of claim 65, wherein said monitoring and/or imaging is provided by an imaging system, including at least one of a magnetic resonance imager, a CT scanner, a fluoroscope, a bi-planar fluoroscope, a PET scanner, and a nuclear medicine camera.

67. The method of claim 58, further comprising withdrawing unused portions of the diagnostic or therapeutic solid agent from the one or more locations of the subject.

68. The method of claim 58, further comprising withdrawing materials other than the diagnostic or therapeutic solid agent from the one or more locations of the subject.

69. The method of claim 58, further comprising co-formulating the diagnostic or therapeutic solid agent with another diagnostic or therapeutic agent.

70. The method of claim 58, wherein the diagnostic or therapeutic solid agent is a carmustine material.

71. The method of claim 58, wherein said delivery further comprises delivering applications to the one or more locations of the subject including at least one of deep electrodes or a sustained release device.

72. The method of claim 58, wherein the one or more locations of the subject comprises at least a portion of an organ.

73. The method of claim 58, where the one or more locations of the subject comprises at least a portion of a tubular structure.

74. The method of claim 73, wherein said tubular structure comprises a blood vessel.

* * * * *